(12) United States Patent
Albert et al.

(10) Patent No.: US 7,902,175 B2
(45) Date of Patent: Mar. 8, 2011

(54) AMINOPROPANOL DERIVATIVES

(75) Inventors: Rainer Albert, Basel (CH); Eric Francotte, Nuglar (CH); Frederic Zecri, Bartenheim (FR); Markus Zollinger, Mohlin (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/391,298

(22) Filed: Feb. 24, 2009

(65) Prior Publication Data

US 2009/0156556 A1 Jun. 18, 2009

Related U.S. Application Data

(62) Division of application No. 10/569,696, filed as application No. PCT/EP2004/009589 on Aug. 27, 2004, now Pat. No. 7,528,120.

(30) Foreign Application Priority Data

Aug. 28, 2003 (GB) .................................. 0320196.9
Oct. 15, 2003 (GB) .................................. 0324206.2

(51) Int. Cl.
*A61K 31/675* (2006.01)
*A61K 31/661* (2006.01)
*C07F 9/572* (2006.01)
*C07F 9/06* (2006.01)

(52) U.S. Cl. .............. 514/80; 514/114; 548/414; 564/15

(58) Field of Classification Search .................. 514/114; 564/15

See application file for complete search history.

(56) References Cited

U.S. PATENT DOCUMENTS

| 6,437,165 B1 | 8/2002 | Mandala et al. |
| 7,173,058 B2 | 2/2007 | Muller et al. |
| 2005/0026976 A1 | 2/2005 | Curtin et al. |

FOREIGN PATENT DOCUMENTS

| JP | 2005-538169 | 12/2005 |
| JP | 2006-524660 | 11/2006 |
| WO | 02/18395 | 3/2002 |
| WO | 02/076995 | 10/2002 |
| WO | 2004/024673 | 3/2004 |

OTHER PUBLICATIONS

Maiereanu, C. et al., Ring-chain tautomerism and other versatile behaviour of 1,4-dimino-and 1,2-phenylene derivatives of some C-substituted serinols, 2002, Tetrahedron, 58, 2688.

Mandala et al., "Alterations of Lymphocyte Trafficking by Sphingosine-1-Phosphate Receptor Agonists", Science, vol. 296, No. 556, (2002), pp. 346-349.

*Primary Examiner* — Kamal A Saeed
*Assistant Examiner* — Kristin Bianchi
(74) *Attorney, Agent, or Firm* — Karen DeBenedictis; Jennifer Chapman; Cozette M. McAvoy

(57) ABSTRACT

Compounds of formula I:

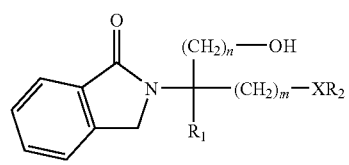

wherein $R_1$, $R_2$, n and m are as defined in the specification, processes for their production, their uses and pharmaceutical compositions containing them.

8 Claims, No Drawings

AMINOPROPANOL DERIVATIVES

This is a divisional of application Ser. No. 10/569,696 filed on Feb. 27, 2006, which is National Stage of International Application No. PCT/EP04/09589 filed on Aug. 27, 2004, which claims benefit of Great Britain Application No. 0320196.9 filed on Aug. 28, 2003, and Great Britain Application No. 0324206.2 filed on Oct. 15, 2003, the entire disclosures of which are hereby incorporated by reference.

The present invention relates to organic compounds, a process for their production and pharmaceutical compositions containing them.

More particularly the present invention provides a compound of formula I:

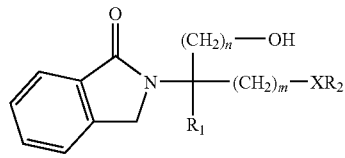

wherein
each of m and n, independently, is 1, 2 or 3;
X is O or a direct bond;
$R_1$ is
- a phenylalkyl wherein alkyl is a straight- or branched ($C_{6-20}$)carbon chain; or
- a phenylalkyl wherein alkyl is a straight- or branched ($C_{1-30}$)carbon chain wherein said phenylalkyl is substituted at the phenyl residue by
  - a straight- or branched ($C_{6-20}$)carbon chain optionally substituted by halogen,
  - a straight- or branched ($C_{6-20}$)alkoxy chain optionally substituted by halogen,
  - a straight- or branched ($C_{6-20}$)alkenyloxy,
  - phenylalkoxy, halophenylalkoxy, phenylalkoxyalkyl, phenoxyalkoxy or phenoxyalkyl,
  - cycloalkylalkyl substituted by $C_{6-20}$alkyl,
  - heteroarylalkyl substituted by $C_{6-20}$alkyl,
  - heterocyclic $C_{6-20}$alkyl or
  - heterocyclic alkyl substituted by $C_{2-20}$alkyl, and wherein
the alkyl moiety may have
  in the carbon chain, a bond or a heteroatom selected from a double bond, a triple bond, O, S, sulfinyl, sulfonyl, or $NR_5$, wherein $R_5$ is H, alkyl, aralkyl, acyl or alkoxycarbonyl, and
  as a substituent alkoxy, alkenyloxy, alkynyloxy, aralkyloxy, acyl, alkylamino, alkylthio, acylamino, alkoxycarbonyl, alkoxycarbonylamino, acyloxy, alkylcarbamoyl, nitro, halogen, amino, hydroxy or carboxy, and
$R_2$ is

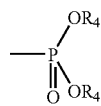

wherein each of $R_3$ and $R_4$, independently, is H or $C_{1-4}$alkyl, wherein alkyl is optionally substituted by 1, 2 or 3 halogen atoms;
In free form or in salt form.

Halogen is F, Cl, Br or I. Alkyl or alkoxy may be straight or branched chain.

Cycloalkyl is preferably $C_{3-10}$cycloalkyl, more preferably $C_{3-6}$cycloalkyl and includes, for example, cyclopropyl, cyclobutyl, cyclopentyl, cyclohexyl or cycloheptyl.

Acyl may be a residue $R_y$—CO— wherein $R_y$ is $C_{1-6}$alkyl, $C_{3-6}$cycloalkyl, phenyl or phenyl-$C_{1-4}$alkyl.

When in the compounds of formula I the carbon chain as $R_1$ is substituted, it is preferably substituted by halogen, nitro, amino, hydroxy or carboxy. When the carbon chain is interrupted by an optionally substituted phenylene, the carbon chain is preferably unsubstituted. When the phenylene moiety is substituted, it is preferably substituted by halogen, nitro, amino, methoxy, hydroxy or carboxy.

In the compounds of the invention, the following significances are preferred individually or in any sub-combination:
1. m and n are each 1 or 2, preferably 1.
2. X is O.
3. $R_1$ is $C_{13-20}$alkyl, optionally substituted by nitro, halogen, amino, hydroxy or carboxy, and, more preferably those wherein $R_1$ is phenylalkyl substituted by $C_{6-14}$-alkyl chain optionally substituted by halogen and the alkyl moiety is a $C_{1-6}$alkyl optionally substituted by hydroxy. More preferably, $R_1$ is phenyl-$C_{1-6}$alkyl, e.g. phenyl-$C_{1-6}$alkyl, e.g. phenyl-$C_2$alkyl, substituted on the phenyl by a straight or branched, preferably straight, $C_{6-14}$alkyl chain. The $C_{6-14}$alkyl chain may be in ortho, meta or para, preferably in para.
4. each of $R_3$ and $R_4$ is H.

A particularly preferred compound is phosphoric acid mono-[2-hydroxymethyl-4-(4-octyl-phenyl)-2-(1 oxo-1,3-dihydro-isoindol-2-yl)-butyl]ester.

Compounds of formula I may exist in free form or in salt form, e.g. addition salts with e.g. inorganic acids, such as hydrochloride, hydrobromide or sulfate, salts with organic acids, such as acetate, fumarate, maleate, benzoate, citrate, malate, methanesulfonate or benzenesulfonate salts; when $R_3$ or $R_4$ is H, $R_2$ may also be present in salt form, e.g. an ammonium salt or salts with metals such as sodium, potassium, calcium, zinc or magnesium, or a mixture thereof. Compounds of formula I and their salts in hydrate or solvate forms are also part of the invention.

The compounds of formula I have one or more asymmetric centers in the molecule, and thus various optical isomers may be obtained. The present invention also encompasses enantiomers, racemates, diastereoisomers and mixtures thereof. The central asymmetric carbon atom may have the R or S configuration. Moreover, when the compounds of formula I include geometric isomers, the present invention embraces cis-compounds, trans-compounds and mixtures thereof. Similar considerations apply in relation to starting materials exhibiting asymmetric carbon atoms or unsaturated bonds as mentioned above.

A compound of formula I may be prepared by reacting a compound of formula II:

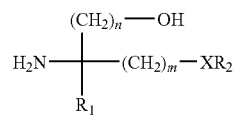

wherein m, n, X, $R_1$ and $R_2$ are as defined in formula 1;

with an aromatic 1,2-dicarbaldehyde, e.g. benzene-1,2-dicarbaldehyde, and recovering the resulting compound of formula I in free or salt form.

The process may be performed according to methods known in the art, e.g. as described in the examples.

A compound of formula II (e.g. a racemic mixture thereof) may be obtained as described in WO 02/18395 or WO 02/076995.

The present invention also provides a compound of formula I or formula II, wherein greater than 70% by weight of the compound is in the form of the S enantiomer, or greater than 70% by weight of the compound is in the form of the R enantiomer, e.g. greater than 90% is in the form of the R or S enantiomer. More preferably greater than 95% by weight, e.g. greater than 99% by weight of the compound is in the form of the R or S enantiomer. Thus the invention may relate to the substantially pure R or S enantiomer (e.g. the S enantiomer substantially free of the R enantiomer or vice versa), preferably the S enantiomer, of a compound of formula 1 or formula II. Particularly preferred are the substantially pure (e.g. greater than 99% by weight) R or S enantiomers, especially the S enantiomers, of phosphoric acid mono-[2-amino-2-hydroxymethyl-4-(4-octyl-phenyl)-butyl]ester (FTY720-phosphate) and phosphoric acid mono-[2-hydroxymethyl-4-(4-octyl-phenyl)-2-(1-oxo-1,3-dihydro-isoindol-2-yl-butyl] ester.

Compounds having the following 3-dimensional configuration are generally preferred:

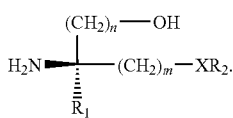

Enantiomers of the compounds of formula I and II cannot be satisfactorily separated by standard methods. According to the present invention, separation of the enantiomers is achieved by the use of novel separation techniques and synthesis strategies.

A compound of formula I, wherein greater than 70% by weight of the compound is in the form of the R or S enantiomer, e.g. the substantially pure R or S enantiomer, may be obtained by:

a) separation of the S enantiomer from the R enantiomer in a racemic mixture of a compound of formula I, using chromatography on a chiral stationary phase; or b) reacting a compound of formula II, wherein greater than 70% by weight of the compound is in the form of the R or S enantiomer, e.g. the substantially pure R or S enantiomer of a compound of formula II, with an aromatic 1,2-dicarbaldehyde e.g. benzene-1,2-dicarbaldehyde.

According to method a), the chromatographic separation is preferably carried out using a chiral ion-exchange phase based on quinine carbamate or quinidine carbamate as chiral selector, e.g. a quinine carbamate phase (8S,9R) available commercially under the tradename ProntoSIL Chiral AX QN-1:

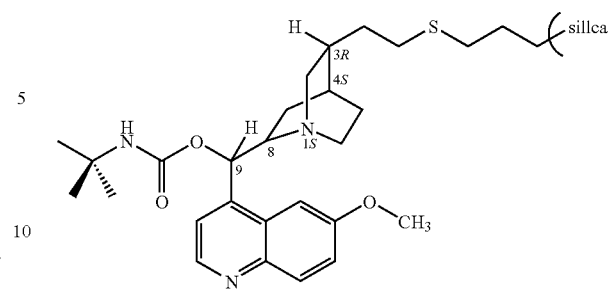

A compound of formula II, wherein greater than 70% by weight of the compound is in the form of the R or S enantiomer, may be obtained by deprotecting a compound of formula III, wherein greater than 70% by weight of the compound of formula III is in the form of the R or S enantiomer:

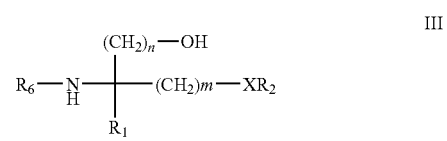

wherein m, n, X, $R_1$ and $R_2$ are as defined above and $R_6$ is an amino protecting group, and, where required, converting the compounds of formula I obtained in free form into the desired salt form, or vice versa.

Examples of suitable amino protecting groups as $R_6$ are e.g. as disclosed in "Protective Groups in Organic Synthesis" T. W. Greene, J. Wiley & Sons NY, $2^{nd}$ ed., chapter 7, 1991, and references therein, e.g. acyl, e.g. tert.-butoxy-carbonyl, benzyloxycarbonyl, 9-fluorenyl methoxy carbonyl, trifluoroacetyl, trimethylsilyethanesulfonyl and the like.

Alternatively and more preferably a compound of formula II, wherein greater than 70% by weight of the compound is in the form of the R or S enantiomer, may be obtained by deprotecting a compound of formula IIIa or IIIb, wherein greater than 70% by weight of the compound of formula IIIa or IIIb is in the form of the R or S enantiomer:

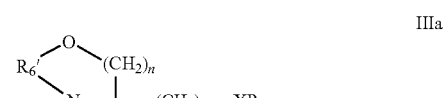

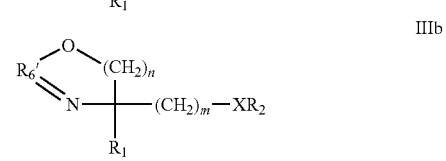

wherein n, m, X, $R_1$ and $R_2$ are as defined above and $R_6'$ is a simultaneous OH and amino protecting group, e.g. such that $R_6'$ together with the O and N atoms to which it is attached, the asymmetric carbon atom and 1 to 3 further carbon atoms forms a cyclic residue, e.g. a 5 to 7-membered heterocyclic ring, e.g oxazolidin-2-one (in IIIa $R_6'$ is —C(O)—) or 2-methyl-4,5-dihydro-oxazole (in IIIb $R_6'$ is —C(CH$_3$)—).

The removal of the $R_6$ or $R_6'$ protecting group in a compound of formula III, IIIa or IIIb may conveniently be performed according to methods known in the art, e.g. by hydrolysis, e.g. in a basic medium, for example using a hydroxide such as barium hydroxide. It may also be performed by hydrogenolysis, e.g. in the presence of Pearlman's catalyst, e.g. as disclosed in J. Org. Chem., 1998, 63, 23752377.

Thus in a further alternative aspect the present invention provides a compound of formula III, IIIa of IIIb as defined above, in free or salt form. The compounds of formula III, IIIa or IIIb have one or more asymmetric centers in the molecule, and thus various optical isomers may be obtained. The present invention also encompasses enantiomers, racemates, diastereoisomers and mixtures thereof.

The removal of the $R_6$ or $R_6'$ protecting group in a compound of formula III, IIIa or IIIb may conveniently be performed according to methods known in the art, e.g. by hydrolysis, e.g. in a basic medium, for example using a hydroxide such as barium hydroxide. It may also be performed by hydrogenolysis, e.g. in the presence of Pearlman's catalyst, e.g. as disclosed in J. Org. Chem., 1998, 63, 2375-2377.

A compound of formula III, IIIa or IIIb comprising greater than 70% by weight of the R or S enantiomer may be obtained by separating the S enantiomer from the R enantiomer in a racemic mixture of a compound of formula III, IIIa or IIIb, using chromatography (MPLC. HPLC, SFC) or simulated moving bed (multi-column) chromatography with a polysaccharide-based chiral stationary phase, preferably an amylose-type phase, e.g. amylose tris[(S)-α-methylbenzyl carbamate coated on silica gel substrate, as available under the tradename CHIRALPAK AS and shown below, or in an immobilized form as prepared according to the processes described in WO 97/04011 and WO 97/49733:

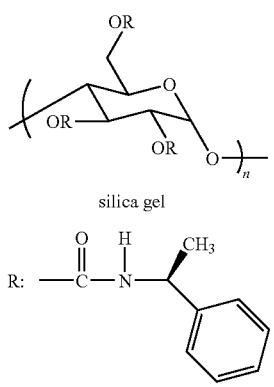

A compound of formula III, IIIa or IIIb comprising greater than 70% by weight of the R or S enantiomer may alternatively be obtained by removing the hydrolysable groups present in $R_2'$ in a compound of formula IV, IVa or IVb comprising greater than 70% by weight of the R or S enantiomer:

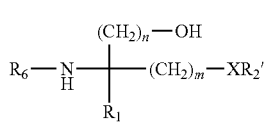

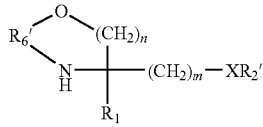

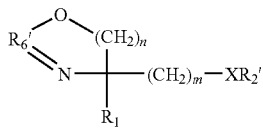

wherein m, n, X, $R_1$, $R_6$ and $R_6'$ are as defined above and $R_2'$ is

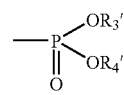

wherein each of $R_3'$ and $R_4'$ is a hydrolysable group.

Preferably $R_3'$ and $R_4'$ are identical and have the significance of e.g. phenyl or benzyl or form together a cyclic system such as in 1,5-dihydro-2,4,3-benzodioxaphosphepin.

A compound of formula IV, IVa or IVb comprising greater than 70% by weight of the R or S enantiomer may be obtained by separating the S enantiomer from the R enantiomer in a racemic mixture of a compound of formula IV, IVa or IVb, e.g. as described above for the separation of enantiomers of compounds of formula III, IIIa or IIIb.

A compound of formula IV, IVa or IVb, e.g. a racemic mixture thereof, wherein X is O may be obtained by reacting a compound of formula V, Va or Vb:

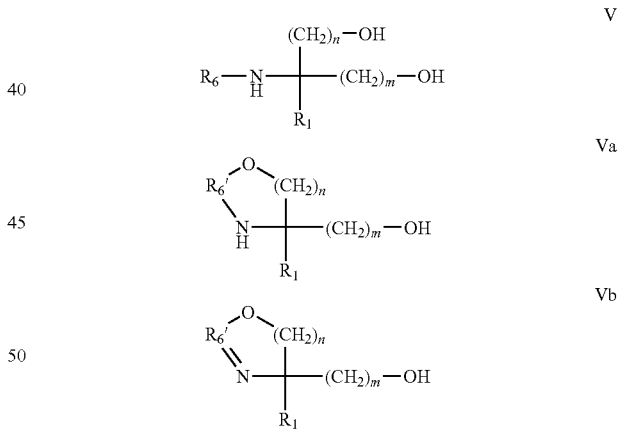

wherein m, n, $R_1$, $R_6$ and $R_6'$ are as defined above, with a phosphorylating agent, e.g. a phosphorochloridate, e.g. diphenylchlorophosphate or dibenzylchlorophosphate, cyanoethylphosphate, a phosphoramidate such as N-phenyl phosphoramidate, 3-(diethylamino)-1,5-dihydro-2,4,3-benzodioxaphosphepin and the like. The reaction may be carried out according to methods known in the art, e.g. as disclosed in J. Org. Chem. supra. In the compounds of formula IIIa the amino group is preferably in protected form, as $R'_4$ when $R_4$ is other than acyl.

A compound of formula IV, IVa or IVb, e.g. a racemic mixture thereof, wherein X is a direct bond may be obtained by reacting a compound of formula V', Va' or Vb':

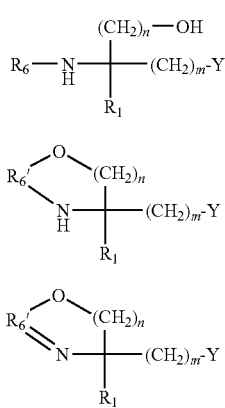

wherein m, n, $R_1$, $R_6$ and $R_6'$ are as defined above, and
Y is a leaving group, e.g. Br,
with a phosphorylating agent, e.g. diethyl phosphite under reducing conditions, e.g. in the presence of NaH. The reaction may be performed in accordance with methods known in the art.

Alternatively the chiral separation may be performed at an earlier stage in the process. Thus a compound of formula IV, IVa or IVb comprising greater than 70% by weight of the R or S enantiomer may be obtained by reacting a compound of formula V, Va, Vb, V', Va' or Vb' comprising greater than 70% by weight of the R or S enantiomer with a phosphorylating agent. A compound of formula V, Va, Vb, V', Va' or Vb' comprising greater than 70% by weight of the R or S enantiomer may be obtained by separating the S enantiomer from the R enantiomer in a racemic mixture of a compound of formula V, Va, Vb, V', Va' or Vb', e.g. using HPLC or simulated moving bed (multi-column) chromatography with a polysaccharide based chiral stationary phase as described above for separation of the enantiomers of a compound of formula IV, IVa or IVb.

A compound of formula V or V' may be prepared by reacting a compound of formula VI:

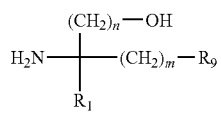

wherein m, n and $R_1$ are as defined above and $R_9$ is OH or a leaving group, e.g. Br,
with an amino protecting group donor compound. A compound of formula Va, Va', Vb or Vb' may be prepared by reacting a compound of formula VI with an OH and amino protecting compound, e.g the OH and amino protection may be performed simultaneously by reacting the free aminoalcohol or aminodiol of formula VI in order to obtain a cyclic residue, e.g. a 5 to 7-membered heterocyclic ring, e.g oxazolidin-2-one or 2-methyl-4,5-dihydro-oxazole, e.g. by reaction with Cbo-Cl, Boc-anhydride, triethylortho acetate and acetonitrile, or phosgene under basic conditions.

At any stage in the process, $R_1$ in any of the formulae above may optionally be converted to an alternative $R_1$ group using known methods. For example, a compound of formula Vb wherein $R_1$ is (4-benzyloxy-phenyl)-ethyl may be converted to an alternative compound of formula Vb wherein $R_1$ is [4-(6-fluoro-hexyloxy)-phenyl]-ethyl by (a) removal of a benzyl group from $R_1$ by hydrogenation to leave a (4-hydroxy-phenyl)-ethyl residue, followed by (b) reaction with 1-bromo-6-fluorohexane. The alternative compound of formula Vb may then undergo chiral separation or be converted to a compound of formula IVb as described above.

The compounds of formulae III, IIIa, IIIb, IV, IVa and IVb comprising greater than 70% by weight of the R or S enantiomer used as starting materials, and salts thereof are also novel and form part of the present invention.

In a further alternative aspect, a compound of formula II wherein greater than 70% by weight of the compound is in the form of the R or S enantiomer, may be obtained by deprotecting and hydrolyzing a compound of formula VII, wherein greater than 70% by weight of the compound is in the form of the R or S enantiomer

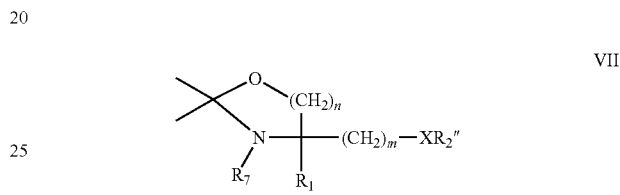

wherein m, n, X and $R_1$ are as defined above, and $R_2''$ is

wherein each of $R_3'$ and $R_4'$ is a hydrolysable group, e.g. tert-butyl, and $R_7$ is an amino protecting group, e.g. benzyloxycarbonyl.

A compound of formula VII, wherein greater than 70% by weight of the compound is in the form of the R or S enantiomer, may be obtained by reacting a compound of formula VIII, wherein greater than 70% by weight of the compound is in the form of the R or S enantiomer,

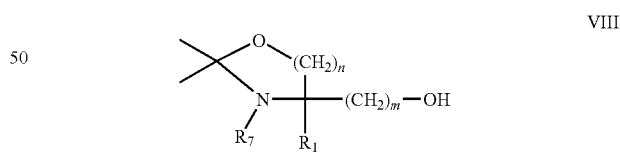

with a phosphorylating agent, e.g. as described above.

Insofar as the production of the starting materials is not particularly described, the compounds are known or may be prepared analogously to methods known in the art or as disclosed in the Examples hereinafter.

The following Examples are illustrative of the invention.

RT=room temperature

CBO=benzyloxycarbonyl

FTY720=2-amino-2-[2-(4-octylphenyl)ethyl]propane-1,3-diol

EDTA=ethylenediaminetetraacetic acid
OPA=ortho-phthalaldehyde (benzene-1,2-dicarbaldehyde)

EXAMPLE 1

Phosphoric Acid mono-[(R/S)-2-hydroxymethyl-4-(4-octyl-phenyl)-2-(1-oxo-1,3-dihydro-isoindol-2-yl)-butyl]ester

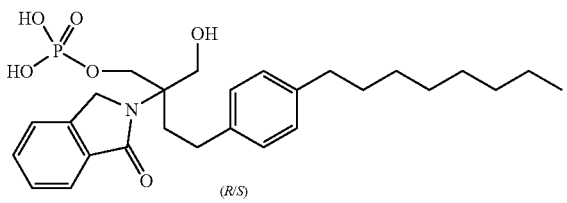

(R/S)

a) (R/S)-4-Hydroxymethyl-4-[2-(4-octyl-phenyl)-ethyl]-oxazolidin-2-one

Benzyl chloroformate (0.45 ml; 3.2 mmol) is added to a suspension of FTY720.HCl (1.03 g, 3 mmol) in 2N NaOH (20 ml). The reaction is kept at RT over night and in order to complete the reaction further benzyl chloroformate (0.9 ml; 6.4 mmol) is added. After 2 days at RT the reaction is acidified with 1N HCl, extracted with methylenechloride and purified on a silica gel column using methylenechloride/methanol/acetic acid$_{50\%}$ (9/1/0.125) as mobile phase.
[M+H]$^+$: 334 (ESI-MS)

b) (R/S)-4-[2-(4-Octyl-phenyl)-ethyl]-4-(3-oxo-1,5-dihydro-3lambda*5*-benzo[e][1,3,2]dioxaphosphepin-3-yloxymethyl)-oxazolidin-2-one To a solution of the endproduct of a) (2.4 g; 7.2 mmol) in methylenechloride/THF 1/1 (100 ml) at 0° C. is added tetrazole (recrystallized; 2.52 g; 36 mmol) and 3-(diethylamino)-1,5-dihydro-2,4,3-benzodioxaphosphepintriphenyl-phosphite (5.17 g; 21.6 mmol). After 18 hours at RT, $H_2O_2$ (8.2 ml [30% in water]; 72 mmol) is added (cooling) to the solution and kept at RT for additional 90 minutes. After quenching with saturated $Na_2S_2O_3$ solution (100 ml) the reaction is extracted with ethylacetate (three times). The organic layer is dried over $Na_2SO_4$ and the compound is purified on silica gel using cyclohexane/ethylacetate 1/1 as mobile phase.

c) Phosphoric Acid mono-{(R/S)-4-[2-(4-octyl-phenyl)-ethyl]-2-oxo-oxazolidin-4-ylmethyl}ester The endproduct of step b) (1.03 g; 2 mmol) is hydrogenated at normal pressure (Pd/C$_{10\%}$; 50 mg) over a period of 90 minutes. After filtration the reaction is concentrated and used in step d) without further purification.

d) Phosphoric Acid mono-[(R/S)-2-amino-2-hydroxymethyl-4-(4-octyl-phenyl)-butyl]ester ((R/S-FTY720-phosphate)

To a solution of the endproduct of step c) in ethanol (20 ml) LiOH (20 ml; 10% solution in water) is added. After 24 hours at reflux the reaction is neutralized with HCl (1N in water) and concentrated. The residue is treated with glacial acetic acid (5 ml) and precipitation of the endproduct occurs after addition water (50 ml). After filtering, washing (water) and drying pure endproduct is obtained without any further purification.

e) Phosphoric Acid mono-[(R/S)-2-hydroxymethyl-4-(4-octyl-phenyl)-2-(1-oxo-1,3-dihydro-isoindol-2-yl)-butyl]ester (OPA-Derivatization)

The endproduct of step d) ((R/S)-FTY720-phosphate) (50 mg; 0.125 mmol) is suspended in a solution of EDTA (0.5 ml; 10 mM in water) and aqueous boric acid (0.5 ml; 3% in water; adjusted to pH 10.5 with aqueous KOH$_{10\%}$). After addition of OPA (33 mg, 0.25 mmol), dissolved in ethanol (0.5 ml), the reaction is kept at RT for 1 hour (ultrasound). After that the pH is adjusted to 3.5 (aqueous HCl; 1N) and extracted with ethylacetate (three times). The organic layer is dried over $Na_2SO_4$ and the compound is purified on silica gel using methylenechloride/methanol (95/5→0/100) as mobile phase.
[M−H]$^-$: 502.5 (ESI-MS)

EXAMPLE 2

Phosphoric Acid mono-[(R)-2-hydroxymethyl-4-(4-octyl-phenyl)-2-(1-oxo-1,3-dihydro-isoindol-2-yl)-butyl]ester

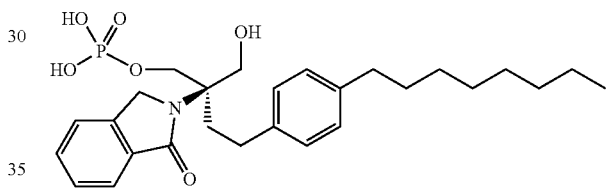

Example 2 is obtained after separation of the final product of step b) by HPLC on CHIRALPAK AS column at a preparative scale (ethanol/n-hexane 40/60 as mobile phase), or by simulated moving bed chromatography on HPLC columns packed with immobilized amylose tris[(S)-α-methylbenzyl carbamate coated on silica gel (n-hexane/ethanol/chloroform 60/20/20 as the mobile phase; feed concentration, 1%) and applying steps c), d) and e) as described for example 1.

EXAMPLE 3

Phosphoric Acid mono-[(S)-2-hydroxymethyl-4-(4-octyl-phenyl)-2-(1-oxo-1,3-dihydro-isoindol-2-yl)-butyl]ester

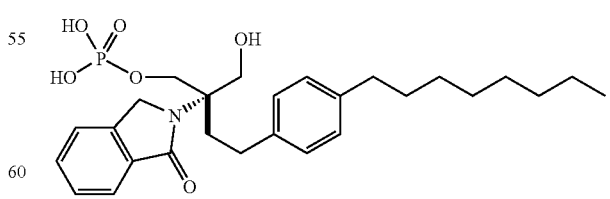

Example 3 is obtained after separation of the final product of step b) by HPLC on CHIRALPAK AS column at a preparative scale (ethanol/n-hexane 40/60 as mobile phase), or by simulated moving bed chromatography on HPLC columns packed with immobilized amylose tris[(S)-α-methylbenzyl carbamate coated on silica gel (n-hexane/ethanol/chloroform 60/20/20 as the mobile phase; feed concentration, 1%) and applying steps c), d) and e) as described for example 1.

EXAMPLE 4

((R/S)-4-{2-[4-(6-Fluoro-hexyloxy)-phenyl]-ethyl}-2-methyl-4,5-dihydro-oxazol-4-yl)-methanol a) To a solution of 4-(2-hydroxy-ethyl)-phenol (50 g, 0.36 mol) in ethanol (400 ml) is added potassium carbonate (75 g, 0.54 mol, 1.5 eq) and benzyl bromide (47.2 ml, 0.39 mol, 1.1 eq), the reaction mixture is stirred at RT overnight. The reaction mixture is then filtered off through celite and concentrated under vacuum. 2-(4-Benzyloxy-phenyl)-ethanol is isolated after crystallization with diethyl ether.

b) To a solution of 2-(4-benzyloxy-phenyl-ethanol (78.72 g, 0.34 mol) in methylene chloride (400 ml) is added triethylamine (67.3 ml, 0.44 mol, 1.4 eq), then at 0° C. is added mesylchloride (34.8 ml, 0.44 mol, 1.3 eq). The reaction mixture is stirred at 0° C. for 30 minutes and allowed to rise to RT. The reaction mixture is extracted with methylene chloride (2×300 ml), the combined organic layers are then washed with brine (2×300 ml) and concentrated under vacuum.

c) To the crude product in solution in ethyl acetate (600 ml) is added sodium iodide (67.2 g, 0.44 mol, 1.3 eq) and the reaction mixture is stirred under reflux for 6 hours. After filtration, the organic layer is washed with brine (3×400 ml), dried with Na$_2$SO$_4$, filtered and concentrated under vacuum. 1-Benzyloxy-4-(2-iodo-ethyl)-benzene is isolated after crystallization with diethyl ether.

d) To a solution of acetamidomalonate (59.4 g, 0.27 mol, 2 eq) in dry dimethylformamide (400 ml) is added at 0° C. under inert atmosphere sodium hydride (60% in oil) (9.94 g, 0.49 mol, 1.8 eq), the reaction mixture is stirred for 3 hours at 0° C. 1-Benzyloxy-4-(2-iodo-ethyl)-benzene (46.8 g, 0.13 mol, 1 eq) in solution in dry dimethylformamide (250 ml) is then slowly added at 0° C. and the reaction mixture is stirred at RT overnight. The reaction mixture is quenched with few drops of methanol and concentrated almost to dryness under vacuum, then extracted with ethyl acetate and washed subsequently with 1N HCl (2×500 ml), saturated solution of NaHCO$_3$ (2×500 ml) and brine (2×500 ml), dried with Na$_2$SO$_4$, filtered and concentrated under vacuum. 2-Acetylamino-2-[2-(4-benzyloxy-phenyl)-ethyl]-malonic acid diethyl ester is isolated after multiple crystallization using diethyl ether.

e) To a solution of 2-acetylamino-2-[2-(4-benzyloxy-phenyl)-ethyl]-malonic acid diethyl ester (44.1 g, 0.1 mol) in ethanol water (2/1) (285 ml/285 ml) is added CaCl$_2$ (28.5 g, 0.26 mol, 2.5 eq) and NaBH$_4$ by portion (19.4 g, 0.52 mol, 5.0 eq), the reaction mixture is stirred overnight at RT. At 0° C. the reaction mixture is carefully quenched with drop wise methanol (10 ml) and concentrated to almost dryness under vacuum. The crude mixture is extracted with ethyl acetate (4×500 ml) and washed subsequently with 1N HCl (2×300 ml), saturated solution of NaHCO$_3$ (2×300 ml) and brine (2×300 ml). The combined organic layers are then dried with Na$_2$SO$_4$, filtered and concentrated under vacuum. N-[3-(4-Benzyloxy-phenyl)-1,1-bis-hydroxymethyl-propyl]-acetamide is carried on without further purification.

f) To a solution of crude N-[3-(4-benzyloxy-phenyl)-1,1-bis-hydroxymethyl-propyl]-acetamide in a mixture of tetrahydrofuran, methanol, water (1/2/2) (450 ml/1900 ml 1900 ml) is added at RT lithium hydroxide (32.7 g, 1.36 mol, 8.0 eq). The reaction mixture is stirred at 65° C. for 5 hours, then extracted with ethyl acetate (500 ml) and washed with brine (2×300 ml), the combined organic layers are then dried with Na$_2$SO$_4$, filtered and concentrated under vacuum. 2-Amino-2-[2-(4-benzyloxy-phenyl)-ethyl]-propane-1,3-diol is isolated after crystallization using ethyl acetate.

g) To a solution of 2-amino-2-[2-(4-benzyloxy-phenyl)-ethyl]-propane-1,3-diol (31.1 g, 0.10 mol) in acetonitrile (2.38 l) is added triethylortho acetate (17.1 ml, 0.12 mol, 1.2 eq) and acetic acid (5.48 ml, 0.11 mol, 1.1 eq), the reaction mixture is then stirred at 80° C. for 5 hours. The reaction mixture is then concentrated under vacuum, {4-[2-(4-benzyloxy-phenyl)-ethyl]-2-methyl-4,5-dihydro-oxazol-4-yl}-methanol is isolated after crystallization with ethyl acetate.

h) To a solution of {4-[2-(4-benzyloxy-phenyl)-ethyl]-2-methyl-4,5-dihydro-oxazol-4-yl}-methanol (26.1 g, 0.08 mol) in methanol (800 ml) is added palladium on charcoal (2.6 g, 10% wt), and the reaction mixture is stirred under hydrogen atmosphere at RT for 5 hours. The reaction mixture is then filtered through celite and concentrated under vacuum. (R/S)-4-[2-(4-Hydroxymethyl-2-methyl-4,5-dihydro-oxazol-4-yl)-ethyl]-phenol is isolated in quantitative yield after crystallization with ethyl acetate and hexanes.

i) To a solution of (R/S)-4-[2-(4-hydroxymethyl-2-methyl-4,5-dihydro-oxazol-4-yl)-ethyl]-phenol (500 mg, 2.12 mmol) in dry DMF (8 ml) is added under inert atmosphere Cs$_2$CO$_3$ (901 mg, 2.76 mmol, 1.3 eq.) and 1-bromo-6-fluorohexane (464.1 mg, 2.55 mmol, 1.2 eq.). The reaction mixture is stirred under inert atmosphere at 85° C. overnight. A saturated solution of NaHCO$_3$ (20 ml) and ethyl acetate (40 ml) are then added. The organic layer is separated and the aqueous phase is extracted with ethyl acetate (3×40 ml). The combined organic extracts are washed with brine and 1M HCl, dried over MgSO$_4$, and evaporated to dryness. Purification by flash chromatography (cy Hexane/ethyl acetate (9/1) to (1/1) and (0/1)) affords (R/S-(4-{2-[4-(6-fluoro-hexyloxy)-phenyl]-ethyl}-2-methyl-4,5-dihydro-oxazol-4-yl)-methanol as colorless oil.

Separation of enantiomers of ((R/S)-4-{2-[4-(6-Fluoro-hexyloxy)-phenyl]-ethyl}-2-methyl-4,5-dihydro-oxazol-4-yl)-methanol is performed by HPLC on CHIRALPAK AD column at a preparative scale (n-hexane/2-propanol 96/6 as the mobile phase).

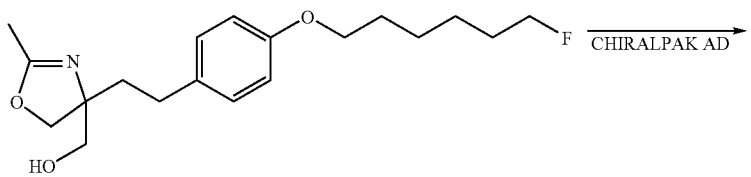

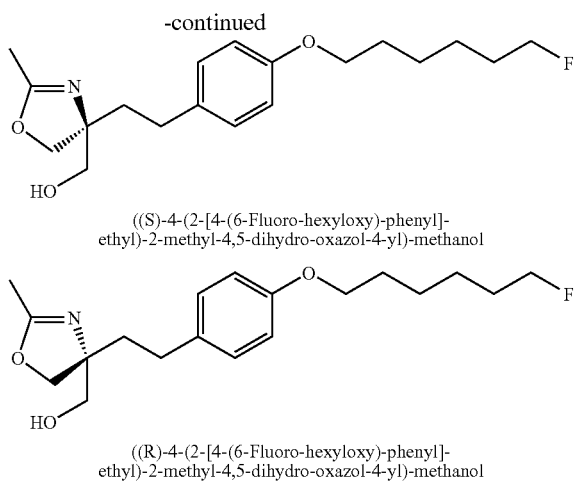

((S)-4-(2-[4-(6-Fluoro-hexyloxy)-phenyl]-
ethyl)-2-methyl-4,5-dihydro-oxazol-4-yl)-methanol ((R)-4-(2-[4-(6-Fluoro-hexyloxy)-phenyl]-
ethyl)-2-methyl-4,5-dihydro-oxazol-4-yl)-methanol

EXAMPLE 5

Phosphoric Acid mono-{(S)-2-amino-4-[4-(6-fluoro-hexyloxy)-phenyl]-2-hydroxymethyl-butyl}ester

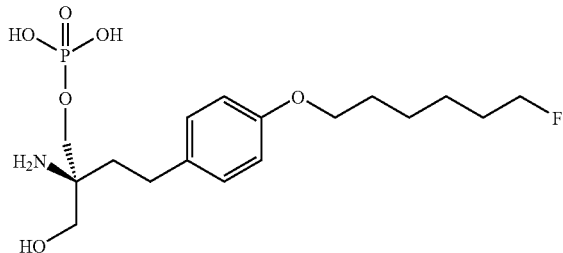

a) To a solution of chiral ((S)-4-{2-[4-(6-fluoro-hexyloxy)-phenyl]-ethyl}-2-methyl-4,5-dihydro-oxazol-4-yl)-methanol (300 mg, 0.80 mmol) and tetrazole (337.4 mg, 4.82 mmol, 6 eq., recrystallized from toluene) in dry THF (6 ml) at −25° C. is added 3-diethylamino-1,5-dihydro-benzo[e][1,3,2]dioxaphosphepine (433.5 µL, 1.56 mmol, 1.95 eq.). The reaction mixture is stirred under argon at −25° C. for 3 h, then allowed to come back to RT. Then, $H_2O_2$ (30%, 75 µL, 4.0 mmol, 5 eq.) is injected at 0° C. with vigorous stirring. The reaction mixture is stirred for further 30 min, followed by addition of saturated sodium thiosulfate solution (1 ml). The organic layer is separated and the aqueous phase is extracted with ether (3×20 ml). The combined organic extracts are washed with brine, dried over $MgSO_4$, and evaporated to dryness. Purification by flash chromatography (ethyl acetate) affords phosphoric acid di-tert-butyl ester (S)-4-{2-[4-(6-fluoro-hexyloxy)-phenyl]-ethyl}-2-methyl-4,5-dihydro-oxazol-4-ylmethyl ester as colorless oil.

b) To a solution of phosphoric acid di-tertbutyl ester (S)-4-{2-[4-(6-fluoro-hexyloxy)-phenyl]-ethyl}-2-methyl-4,5-dihydro-oxazol-4-ylmethyl ester (33 mg, 0.050 mmol) in ethanol (2 ml) is added conc. HCl (2 ml). The reaction mixture is stirred at 85° C. for 2 hours, then concentrated to dryness. The residue is re-dissolved in ethyl acetate and precipitated with hexanes. The solid is filtered off, washed with dry ether and dried under vacuum to afford phosphoric acid mono-{(S)-2-amino-4-[4-(6-fluoro-hexyloxy)-phenyl]-2-hydroxymethyl-butyl}ester as a colorless powder.

EXAMPLE 6

Phosphoric Acid mono-{(R)-2-amino-4-[4-(6-fluoro-hexyloxy)-phenyl]-2-hydroxymethyl-butyl}ester

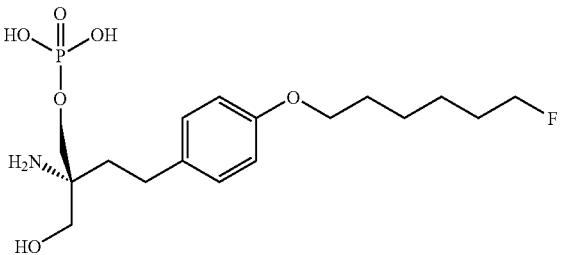

The synthesis is performed applying the chemistry described for example 5.

EXAMPLE 7

Phosphoric Acid mono-[(S)-4-[4-(6-fluoro-hexyloxy)-phenyl]-2-hydroxymethyl-2-(1-oxo-1,3-dihydro-isoindol-2-yl)-butyl]ester

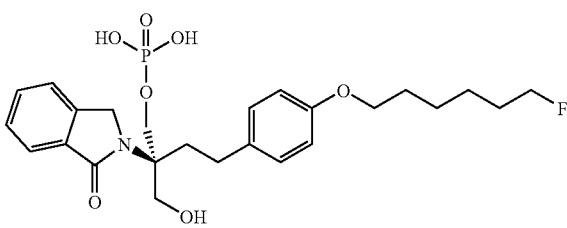

OPA-derivatization is performed according to the procedure given in example 1, step e.

EXAMPLE 8

Phosphoric Acid mono-[(R)-4-[4-(6-fluoro-hexyloxy)-phenyl]-2-hydroxymethyl-2-(1-oxo-1,3-dihydro-isoindol-2-yl)-butyl]ester

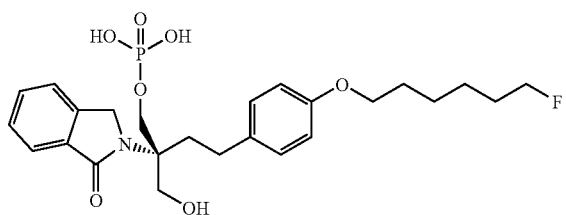

OPA-derivatization is performed according to the procedure given in example 1, step e.

EXAMPLE 9

Phosphoric Acid mono-((R)-2-amino-4-{4-[2-(3-fluoro-phenoxy)-ethoxy]-phenyl}-2-hydroxymethyl-butyl)ester

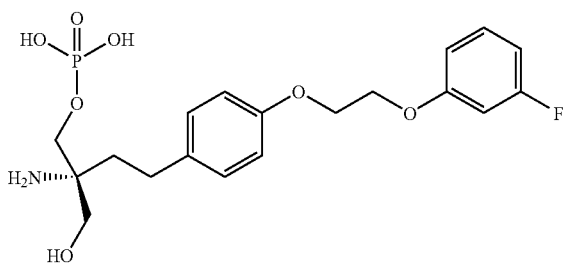

To a solution of 4-(2-hydroxy-ethyl)-phenol (50 g, 0.36 mol) in ethanol (400 ml) is added potassium carbonate (75 g, 0.54 mol, 1.5 eq) and benzyl bromide (47.2 ml, 0.39 mol, 1.1 eq), the reaction mixture is stirred at room temperature overnight. The reaction mixture is then filtered off trough celite and concentrated under vacuum. 2-(4-Benzyloxy-phenyl)-ethanol is isolated after crystallization with diethyl ether (82.6 g, 95%).

To a solution of 2-(4-benzyloxy-phenyl)-ethanol (78.72 g, 0.34 mol) in methylene chloride (400 ml) is added triethylamine (67.3 ml, 0.44 mol, 1.4 eq), then at 0° C. is added mesylchloride (34.8 ml, 0.44 mol, 1.3 eq). The reaction mixture is stirred at 0° C. for 30 minutes and allowed to rise to room temperature. The reaction mixture is extracted with methylene chloride (2×300 ml), the combined organic layers are then washed with brine (2×300 ml) and concentrated under vacuum. To the crude product in solution in ethyl acetate (600 ml) is added sodium iodide (67.2 g, 0.44 mol, 1.3 eq) and the reaction mixture is stirred under reflux for 6 hours. After filtration, the organic layer is washed with brine (3×400 ml), dried with $Na_2SO_4$, filtered and concentrated under vacuum. 1-Benzyloxy-4-(2-iodo-ethyl)-benzene is isolated after crystallization with diethyl ether (116.5 g, 86%).

To a solution of acetamidomalonate (59.4 g, 0.27 mol, 2 eq) in dry dimethylformamide (400 ml) is added at 0° C. under inert atmosphere sodium hydride (60% in oil) (9.94 g, 0.49 mol, 1.8 eq), the reaction mixture is stirred for 3 hours at 0° C. 1-Benzyloxy-4-(2-iodo-ethyl)-benzene (46.8 g, 0.13 mol, 1 eq) in solution in dry dimethylformamide (250 ml) is then slowly added at 0° C. and the reaction mixture is stirred at room temperature overnight. The reaction mixture is quenched with few drops of methanol and concentrated almost to dryness under vacuum, then extracted with ethyl acetate and washed subsequently with 1N HCl (2×500 ml), saturated solution of $NaHCO_3$ (2×500 ml) and brine (2×500 ml), dried with $Na_2SO_4$, filtered and concentrated under vacuum. 2-Acetylamino-2-[2-(4-benzyloxy-phenyl)-ethyl]-malonic acid diethyl ester is isolated after multiple crystallization using diethyl ether (47.3 g, 80%).

To a solution of 2-acetylamino-2-[2-(4-benzyloxy-phenyl)-ethyl]-malonic acid diethyl ester (44.1 g, 0.1 mol) in ethanol water (2/1) (285 ml/285 ml) is added $CaCl_2$ (28.5 g, 0.26 mol, 2.5 eq) and $NaBH_4$ by portion (19.4 g, 0.52 mol, 5.0 eq), the reaction mixture is stirred overnight at room temperature. At 0° C. the reaction mixture is carefully quenched with drop wise methanol (10 ml) and concentrated to almost dryness under vacuum. The crude mixture is extracted with ethyl acetate (4×500 ml) and washed subsequently with 1N HCl (2×300 ml), saturated solution of $NaHCO_3$ (2×300 ml) and brine (2×300 ml). The combined organic layers are then dried with $Na_2SO_4$, filtered and concentrated under vacuum. N-[3-(4-Benzyloxy-phenyl)-1,1-bis-hydroxymethyl-propyl]-acetamide is carried on without further purification.

To a solution of crude N-[3-(4-benzyloxy-phenyl)-1,1-bis-hydroxymethyl-propyl]-acetamide in a mixture of tetrahydrofuran, methanol, water (1/2/2) (450 ml/900 ml/900 ml) is added at room temperature lithium hydroxide (32.7 g, 1.36 mol, 8.0 eq). The reaction mixture is stirred at 55° C. for 5 hours, then extracted with ethyl acetate (500 ml) and washed with brine (2×300 ml), the combined organic layers are then dried with $Na_2SO_4$, filtered and concentrated under vacuum. 2-Amino-2-[2-(4-benzyloxy-phenyl)-ethyl]-propane-1,3-diol is isolated after crystallization using ethyl acetate (28.8 g, 97%).

To a solution of 2-amino-2-[2-(4-benzyloxy-phenyl)-ethyl]-propane-1,3-diol (200 mg, 0.66 mmol) in dioxane (10 ml) is added a solution of 1M NaOH (0.73 ml, 073 mmol, 1.1 eq) and Boc anhydride (217 mg, 0.99 mmol, 1.5 eq). The reaction mixture is then stirred overnight at room temperature. Extraction with ethyl acetate (80 ml) and washed with brine (2×50 ml), the combined organic layers are then dried with $Na_2SO_4$, filtered and concentrated under vacuum. 2-Amino-2-[2-(4-benzyloxy-phenyl)-ethyl]-propane-1,3-diol is isolated as a white solid after flash chromatography (Ethyl acetate/Hexane (3/1)) and crystallization with diethyl ether (204 mg, 87%).

To a solution of 2-amino-2-[2-(4-benzyloxy-phenyl)-ethyl]-propane-1,3-diol (6.31 g, 0.16 mol) in dichloromethane (120 ml) and pyridine (1.26 ml, 0.16 mol) is added at room temperature o-nitrobenzoylchloride (2.27 ml. 0.017 mol). The reaction mixture is then stirred overnight at room temperature. Extraction with dichloromethane (300 ml) and washed with brine (2×200 ml), the combined organic layers are then dried with $Na_2SO_4$, filtered and concentrated under vacuum. 2-Nitro-benzoic acid 4-(4-benzyloxy-phenyl)-2-tert-butoxycarbonylamino-2-hydroxymethyl-butyl ester is isolated as a white solid after flash chromatography (Ethyl acetate/Hexane (1/1)) and crystallization with diethyl ether (6.55 mg, 76%). 1.40 g of starting material could be isolated.

To a solution of 2-nitro-benzoic acid 4-(4-benzyloxy-phenyl)-2-tert-butoxycarbonylamino-2-hydroxymethyl-butyl ester (105 mg, 0.19 mmol) in toluene (2 ml) is added 2.2 dimethoxypropane (0.06 ml, 0.57 mmol, 3 eq) and a catalytic amount of p-toluene sulfonic acid. The reaction mixture is stirred at 95° C. for 6 hours, then concentrated to dryness under negative pressure. 4-[2-(4-Benzyloxy-phenyl)-ethyl]-2,2-dimethyl-4-(2-nitro-benzoyloxy-methyl)-oxazolidine-3-carboxylic acid tert-butyl ester is isolated as an oil (88 mg, 78%) after purification by flash chromatography (Ethyl acetate/Hexane (1/3)).

To a solution of 4-[2-(4-benzyloxy-phenyl)-ethyl]-2,2-dimethyl-4-(2-nitro-benzoyloxymethyl)-oxazolidine-3-carboxylic acid tert-butyl ester (80 mg, 0.13 mmol) in methanol (1 ml) and THF (1 ml) is added K$_2$CO$_3$ (1.5 mg, 0.076 eq), the reaction mixture is stirred overnight at room temperature. The reaction mixture is concentrated to dryness and 4-[2-(4-benzyloxy-phenyl)-ethyl]-4-hydroxymethyl-2,2-dimethyl-oxazolidine-3-carboxylic acid tert-butyl ester (51 mg, 85%) is isolated as a white solid after flash chromatography (Ethyl acetate/Hexane (1/4)).

To a solution of 4-[2-(4-benzyloxy-phenyl)-ethyl]-4-hydroxymethyl-2,2-dimethyl-oxazolidine-3-carboxylic acid tert-butyl ester (25 mg, 0.05 mmol) in methanol (10 ml) is added a catalytic amount of palladium on charcoal (10% wt). The reaction mixture is stirred under H$_2$ atmosphere at room temperature for 2 hours. 4-Hydroxymethyl-4-[2-(4-hydroxyphenyl)-ethyl]-2,2-dimethyl-oxazolidine-3-carboxylic acid tert-butyl ester is isolated as a white solid after filtration of the suspension through celite and concentration to dryness.

To a solution of (S)-4-hydroxymethyl-4-[2-(4-hydroxyphenyl)-ethyl]-2,2-dimethyl-oxazolidine-3-carboxylic acid tert-butyl ester (100 mg, 0.28 mmol) in DMF (5 ml) is added CsCO$_3$ (120.5 mg, 0.37 mmol, 1.3 eq) and 1-(2-bromo-ethoxy)-3-fluoro-benzene (80.7 mg, 0.37 mmol, 1.3 eq). The reaction mixture is stirred at 85° C. for 4 hours. Ethyl acetate and water are then added, the organic layer is separated and the aqueous phase is extracted with ethylacetate (3×50 ml). The combined organic extracts are washed with brine, dried over MgSO$_4$, and evaporated to dryness. Purification by flash chromatography (AcOEt/Hx 9:1) affords (S)-4-(2-{4-[2-(3-fluoro-phenoxy)-ethoxy]-phenyl}-ethyl)-4-hydroxymethyl-2,2-dimethyl-oxazolidine-3-carboxylic acid tert-butyl ester as colorless oil.

To a solution of (S)-4-(2-{4-[2-(3-fluoro-phenoxy)-ethoxy]-phenyl}-ethyl)-hydroxymethyl-2,2-dimethyl-oxazolidine-3-carboxylic acid tert-butyl ester (70 mg, 0.14 mmol) and tetrazole (49 mg, 0.7 mmol, 5 eq., recrystallized from toluene) in dry THF (5 ml) is added di-tBu-N,N-diisopropylphosphoramide (155 mg, 0.56 mmol, 4 eq.). After stirring under argon at RT for 3 h, H$_2$O$_2$ (30%, 10 eq.) is slowly added at 0° C. with vigorous stirring. The reaction mixture is stirred for further 30 min, followed by addition of saturated sodium thiosulfate solution (5 ml). The organic layer is separated and the aqueous phase is extracted with ether (3×20 ml). The combined organic extracts are washed with brine, dried over MgSO$_4$, and evaporated to dryness. Purification by flash chromatography (AcOEt/Hx 1:1) affords (R)-4-(di-tert-butoxy-phosphoryloxymethyl)-4-(2-{4-[2-(3-fluoro-phenoxy)-ethoxy]-phenyl}-ethyl)-2,2-dimethyl oxazolidine-3-carboxylic acid tert-butyl ester as colorless crystals.

Finally, a solution of (R)-4-(di-tert-butoxy-phosphoryloxymethyl)-4-(2-{4-[2-(3-fluoro-phenoxy)-ethoxy]-phenyl}-ethyl)-2,2-dimethyl-oxazolidine-3-carboxylic acid tert-butyl ester (70 mg, 0.10 mmol) in conc. HCl (2 ml). Is stirred at room temperature for one hour and is then heated to 95° C. for 2 hours, then concentrated to dryness. The residue is re-dissolved in ethyl acetate and precipitated with hexanes. The solid is filtered off, washed with dry ether and dried in vacuo to afford phosphoric acid mono-((R)-2-amino-4-{4-[2-(3-fluoro-phenoxy)-ethoxy]-phenyl}-2-hydroxymethyl-butyl)ester as a colorless powder.

EXAMPLE 10

Phosphoric Acid mono-((S)-2-amino-4-{4-[2-(3-fluoro-phenoxy)-ethoxy]-phenyl}-2-hydroxymethyl-butyl)ester

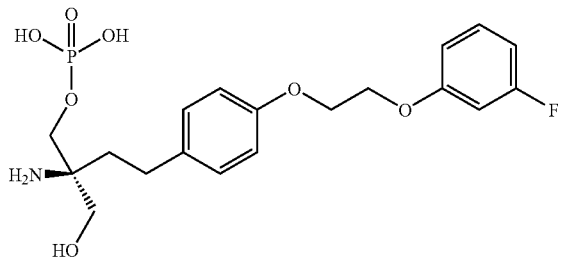

Phosphoric acid mono-((S)-2-amino-4-{4-[2-(3-fluoro-phenoxy)-ethoxy]-phenyl}-2-hydroxymethyl-butyl)ester is prepared as described in example 9 using (R)-4-hydroxymethyl-4-[2-(4-hydroxy-phenyl)-ethyl]-2,2-dimethyl-oxazolidine-3-carboxylic acid tert-butyl ester instead of (S)-4-hydroxymethyl-4-[2-(4-hydroxy-phenyl)-ethyl]-2,2-dimethyl-oxazolidine-3-carboxylic acid tert-butyl ester.

EXAMPLE 11

Phosphoric Acid mono-{(R)-2-amino-2-hydroxymethyl-4-[4-(2-m-tolyloxy-ethoxy)-phenyl]-butyl}ester

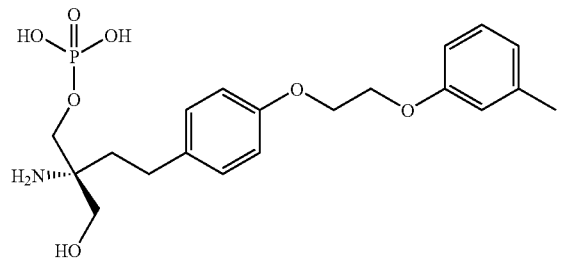

Phosphoric acid mono-{(R)-2-amino-2-hydroxymethyl-4-[4-(2-m-tolyloxy-ethoxy)-phenyl]-butyl}ester is prepared using an analogous method to that described in example 9.

EXAMPLE 12

Phosphoric Acid mono-((R)-2-amino-2-hydroxymethyl-4-{4-[2-(4-methoxy-phenyl)-ethoxy]-phenyl}-butyl)ester

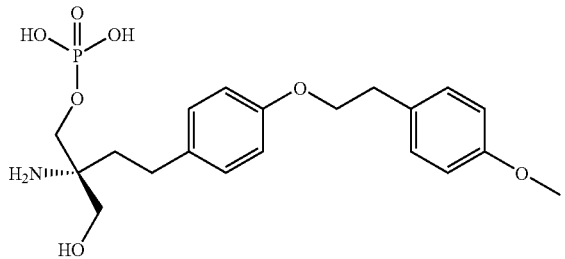

Phosphoric acid mono-((R)-2-amino-2-hydroxymethyl-4-{4-[2-(4-methoxy-phenyl)-ethoxy]-phenyl}-butyl)ester is prepared using an analogous method to that described in example 9.

EXAMPLE 13

Phosphoric Acid mono-{(R)-2-amino-2-hydroxymethyl-4-[4-(2-p-tolyl-ethoxy)-phenyl]-butyl}ester

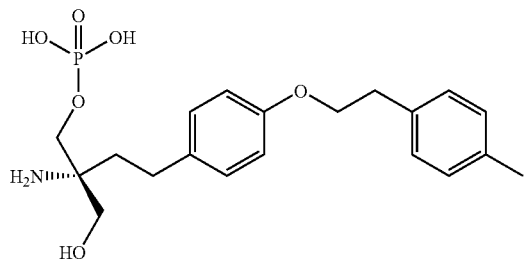

Phosphoric acid mono-{(R)-2-amino-2-hydroxymethyl-4-[4-(2-p-tolyl-ethoxy)-phenyl]-butyl}ester is prepared using an analogous method to that described in example 9.

EXAMPLE 14

Phosphoric Acid mono-((R)-2-amino-2-hydroxymethyl-4-{4-[2-(4-trifluoromethyl-phenyl)-ethoxy]-phenyl}-butyl)ester

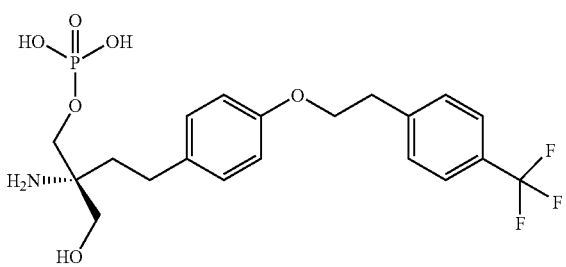

Phosphoric acid mono-((R)-2-amino-2-hydroxymethyl-4-{4-[2-(4-trifluoromethyl-phenyl)-ethoxy]-phenyl}-butyl)ester is prepared using an analogous method to that described in example 9.

EXAMPLE 15

Phosphoric Acid Diethyl Ester 4-(2-{4-[2-(3-fluoro-4-methoxy-phenyl)-ethoxy]-phenyl}-ethyl)-2-methyl-4,5-dihydro-oxazol-4-ylmethyl Ester

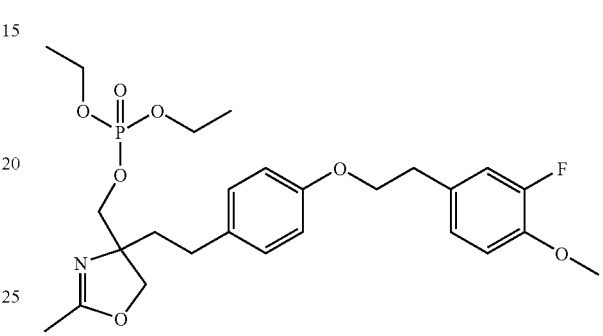

To a solution of phosphoric acid mono-(2-amino-4-{4-[2-(3-fluoro-4-methoxy-phenyl)-ethoxy]-phenyl}-2-hydroxymethyl-butyl)ester (100 mg, 0.22 mmol) in triethyl orthoacetate (5 ml) is added acetic acid (13 ul, 0.22 mmol). The reaction mixture is stirred at 80° C. for 2 hours and concentrated to dryness. Purification by flash chromatography (AcOEt/Hx 1:4) affords phosphoric acid diethyl ester 4-(2-{4-[2-(3-fluoro-4-methoxy-phenyl)-ethoxy]-phenyl}-ethyl)-2-methyl-4,5-dihydro-oxazol-4-ylmethyl ester as colorless oil.

EXAMPLE 16

Phosphoric Acid Diethyl Ester (S)-2-methyl-4-[2-(4-octyl-phenyl)-ethyl]-4,5-dihydro-oxazol-4-ylmethyl Ester

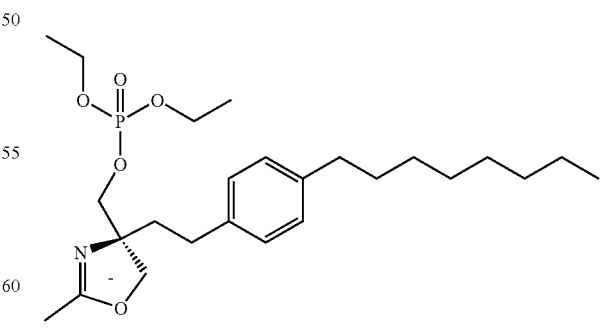

Phosphoric acid diethyl ester (S)-2-methyl-4-[2-(4-octyl-phenyl)-ethyl]-4,5-dihydro-oxazol-4-ylmethyl ester is prepared as described in example 15 using of phosphoric add mono-(2-amino-4-{4-[2-(3-fluoro-4-methoxy-phenyl)-ethoxy]-phenyl}-2-hydroxymethyl-butyl)ester.

EXAMPLE 17

Phosphoric Acid Diethyl Ester (R)-2-methyl-4-[2-(4-octyl-phenyl)-ethyl]-4,5-dihydro-oxazol-4-ylmethyl Ester

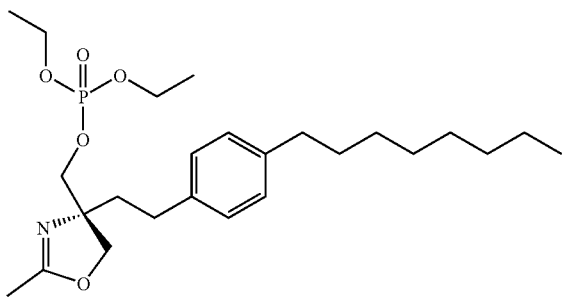

Phosphoric acid diethyl ester (R)-2-methyl-4-[2-(4-octyl-phenyl)-ethyl]-4,5-dihydro-oxazol-4-ylmethyl ester is prepared as described in example 15 using phosphoric acid mono-(2-amino-4-{4-[2-(3-fluoro-4-methoxy-phenyl)-ethoxy]-phenyl}-2-hydroxymethyl-butyl)ester.

EXAMPLE 18

Chromatographic Resolution of Racemic 4-hydroxymethyl-4-[2-(4-hydroxy-phenyl)-ethyl]-2,2-dimethyl-oxazolidine-3-carboxylic Acid tert-butyl Ester 10 micro-liter of a 0.1% ethanol solution of racemic 4-hydroxymethyl-4-[2-(4-hydroxy-phenyl)-ethyl]-2,2-dimethyl-oxazolidine-3-carboxylic acid tert-butyl ester are injected on a Chiralcel OD-H column (0.46×25 cm; commercially available from Chiral Technologies). The chromatographic separation is achieved at room temperature and at a flow rate of 1 ml/min using a mixture of n-hexane/ethanol 90/10 (volume) containing 0.1% trifluoroacetic acid (TFA) as the mobile phase. Detection is performed by UV at 210 nm. The enantiomers elute respectively after 7.23 min and 9.39 min (Separation factor α: 1.52)

EXAMPLE 19

Chromatographic Resolution of Racemic Phosphoric Acid Diethyl Ester 4-(2-{4-[2-(3-fluoro-4-methoxy-phenyl)-ethoxy]-phenyl}ethyl)-2-methyl-4,5-dihydro-oxazol-4-ylmethyl Ester 10 micro-liter of a 0.1% ethanol solution of racemic phosphoric acid diethyl ester 4-(2-{4-[2-(3-fluoro-4-methoxy-phenyl)-ethoxy]-phenyl}ethyl)-2-methyl-4,5-dihydro-oxazol-4-ylmethyl ester are injected on a Chiralcel OD-H column (0.46×25 cm; commercially available from Chiral Technologies). The chromatographic separation is achieved at room temperature and at a flow rate of 1 ml/min using a mixture of n-hexane/ethanol 95/5 (volume) as the mobile phase. Detection is performed by UV at 210 nm. The enantiomers elute respectively after 31.17 min and 35.44 min (Separation factor α: 1.15)

EXAMPLE 20

Chromatographic Separation of the Enantiomers Phosphoric Acid Diethyl Ester 4-(2-{4-[2-(3-fluoro-4-methoxy-phenyl)-ethoxy]-phenyl}ethyl)-2-methyl-4,5-dihydro-oxazol-4-ylmethyl Ester 10 micro-liter of a 0.1% ethanol solution of a mixture of the enantiomers phosphoric acid diethyl ester 4-(2-{4-[2-(3-fluoro-4-methoxy-phenyl)-ethoxy]-phenyl}-ethoxyl)-2-methyl-4,5-dihydro-oxazol-4-ylmethyl ester are injected on a Chiralcel OJ-H column (0.46×25 cm; commercially available from Chiral Technologies). The chromatographic separation is achieved at room temperature and at a flow rate of 1 ml/min using a mixture of n-hexane/2-propanol 75/25 (volume) as the mobile phase. Detection is performed by UV at 210 nm. The enantiomers elute respectively after 13.89 min and 16.77 min (Separation factor α: 1.27)

EXAMPLE 21

Chromatographic Separation of the Enantiomers Phosphoric Acid Diethyl Ester (S)-2-methyl-4-[2-(4-octyl-phenyl)-ethyl]-4,5-dihydro-oxazol-4-ylmethyl Ester 10 micro-liter of a 0.1% ethanol solution of a mixture of the enantiomers phosphoric acid diethyl ester (S)-2-methyl-4-[2-(4-octyl-phenyl)-ethyl]-4,5-dihydro-oxazol-4-ylmethyl ester are injected on a Chiralpak AD-H column (0.46×25 cm; commercially available from Chiral Technologies). The chromatographic separation is achieved at room temperature and at a flow rate of 1 ml/min using a mixture of n-hexane/ethanol 95/5 (volume) as the mobile phase. Detection is performed by UV at 210 nm. The enantiomers elute respectively after 10.35 min and 12.32 min (Separation factor α: 1.27).

The compounds of formula II comprising greater than 70% of the R or S enantiomer, especially the S enantiomer, in free form or in pharmaceutically acceptable salt form, (hereinafter referred to as the compounds of the invention) exhibit valuable pharmacological properties, e.g. lymphocyte recirculation modulating properties, e.g. as indicated in in vitro and in vivo tests and are therefore indicated for therapy.

A. In Vitro

The compounds of the invention have binding affinity to individual human S1P receptors as determined in following assays:

Transient Transfection of Human S1P Receptors into HEK293 Cells

S1P receptors and $G_i$ proteins are cloned, and equal amounts of 4 cDNAs for the S1P receptor, $G_i$-α, $G_i$-β and $G_i$-γ are mixed and used to transfect monolayers of HEK293 cells using the calcium phosphate precipitate method (M. Wigler et al., Cell. 1977; 11; 223 and DS. Im et al., Mol. Pharmacol. 2000; 57; 753). Briefly, a DNA mixture containing 25 μg of DNA and 0.25 M CaCl is added to HEPES-buffered 2 mM $Na_2HPO_4$. Subconfluent monolayers of HEK293 cells are poisoned with 25 mM chloroquine, and the DNA precipitate is then applied to the cells. After 4 h, the monolayers are washed with phosphate-buffered saline and refed media (90% 1:1 Dulbecco's modified essential media (DMEM):F-12+10% fetal bovine serum). The cells are harvested 48-72 h after addition of the DNA by scraping in HME buffer (in mM: 20 HEPES, 5 $MgCl_2$, 1 EDTA, pH 7.4) containing 10% sucrose on ice, and disrupted using a Dounce homogenizer. After centrifugation at 800×g, the supernatant is diluted with HME without sucrose and centrifuged at 100,000×g for 1 h. The resulting pellet is rehomogenized and centrifuged a second hour at 100,000×g. This crude membrane pellet is resuspended in HME with sucrose, aliquoted, and snap-frozen by immersion in liquid nitrogen. The membranes are stored at 70° C. Protein concentration is determined spectroscopically by Bradford protein assay.

GTPγS Binding Assay Using S1P Receptor/HEK293 Membrane Preparations

GTPγS binding experiments are performed as described by D S. Im et al., Mol. Pharmacol. 2000; 57:753. Ligand-mediated GTPγS binding to G-proteins is measured in GTP binding buffer (in mM: 50 HEPES, 100 NaCl, 10 $MgCl_2$, pH 7.5) using 25 μg of a membrane preparation from transiently transfected HEK293 cells. Ligand is added to membranes in the presence of 10 μM GDP and 0.1 nM [$^{35}$S]GTPγS (1200 Ci/mmol) and incubated at 30° C. for 30 min. Bound GTPγS is separated from unbound using the Brandel harvester (Gaithersburg, Md.) and counted with a liquid scintillation counter.

In these assays, the compounds of the invention have binding affinities to S1P receptors in the sub-microM range.

In particular, the $EC_{50}$ values in nM for the following compounds at various S1P receptors are shown in the table below:

| | S1P-1 $EC_{50}$ nM | S1P-3 $EC_{50}$ nM | S1P-2 $EC_{50}$ nM | S1P-4 $EC_{50}$ nM | S1P-5 $EC_{50}$ nM |
|---|---|---|---|---|---|
| (R)-FTY720-P | 191.15 | 28.91 | >10000 | 80.13 | >10000 |
| (S)-FTY720-P | 0.33 | 3.21 | >10000 | 0.75 | 0.33 |
| Ex. 14 | 0.4 | 140 | >10000 | 6.6 | 7.7 | wherein (R)-FTY720-P is (R)-FTY720-phosphate, (S)-FTY720-P is (S)-FTY720-phosphate, in contrast to (R)-FTY720-phosphate, which shows agonistic effects on S1P receptors only at very high concentrations, (S)-FTY720-phosphate is a full agonist on S1P1 and S1P3 and a partial agonist on S1P4 and S1P5 in the low nanomolar range.

B. In Vivo: Blood Lymphocyte Depletion

A compound of the invention or the vehicle is administered orally by gavage to rats. Tail blood for hematological monitoring is obtained on day −1 to give the baseline individual values, and at 2, 6, 24, 48 and 72 hours after drug application. In this assay, the compounds of the invention deplete peripheral blood lymphocytes when administered at a dose of 0.03 to 3 mg/kg.

The compounds of the invention are, therefore, useful in the treatment and/or prevention of diseases or disorders mediated by lymphocytes interactions, e.g. in transplantation, such as acute or chronic rejection of cell, tissue or organ allo- or xenografts or delayed graft function, graft versus host disease, autoimmune diseases, e.g. rheumatoid arthritis, systemic lupus erythematosus, hashimoto's thyroids, multiple sclerosis, myasthenia gravis, diabetes type I or II and the disorders associated therewith, vasculitis, pernicious anemia, Sjoegren syndrome, uveitis, psoriasis, Graves opthalmopathy, alopecia agreata and others, allergic diseases, e.g. allergic asthma, atopic dermatitis, allergic rhinitis/conjunctivitis, allergic contact dermatitis, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, myocarditis or hepatitis, ischemia/reperfusion injury. e.g. myocardial infarction, stroke, gut ischemia, renal failure or hemorrhage shock, traumatic shock, others, cancer, e.g. T cell lymphomas or T cell leukemias, infectious diseases, e.g. toxic shock (e.g. superantigen induced), septic shock, adult respiratory distress syndrome or viral infections, e.g. AIDS, viral hepatitis or chronic bacterial infection. Examples of cell, tissue or solid organ transplants include e.g. pancreatic islets, stem cells, bone marrow, corneal tissue, neuronal tissue, heart, lung, combined heart-lung, kidney, liver, bowel, pancreas, trachea or oesophagus.

For the above uses the required dosage will of course vary depending on the mode of administration, the particular condition to be treated and the effect desired. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, for example, in divided doses up to four times a day or in retard form. Suitable unit dosage forms for oral administration comprise from ca. 1 to 50 mg active ingredient.

The compounds of the invention may be administered by any conventional route, in particular enterally, e.g. orally, e.g. in the form of tablets or capsules, or parenterally, e.g. in the form of injectable solutions or suspensions, topically, e.g. in the form of lotions, gels, ointments or creams, or in a nasal or a suppository form. Pharmaceutical compositions comprising a compound of the invention in free form or in pharmaceutically acceptable salt form in association with at least one pharmaceutical acceptable carrier or diluent may be manufactured in conventional manner by mixing with a pharmaceutically acceptable carrier or diluent.

The compounds of the invention may be administered in free form or in pharmaceutically acceptable salt form e.g. as indicated above. Such salts may be prepared in conventional manner and exhibit the same order of activity as the free compounds.

In accordance with the foregoing the present invention further provides:

1.1 A method for preventing or treating disorders or diseases mediated by lymphocytes, e.g. such as indicated above, in a subject in need of such treatment, which method comprises administering to said subject an effective amount of a compound of formula II comprising greater than 70% by weight of the R or S enantiomer, or a pharmaceutically acceptable salt thereof;

1.2 A method for preventing or treating acute or chronic transplant rejection or T-cell mediated inflammatory or autoimmune diseases, e.g. as indicated above, in a subject in need of such treatment, which method comprises administering to said subject an effective amount of a compound of formula II comprising greater than 70% by weight of the R or S enantiomer, or a pharmaceutically acceptable salt thereof;

2. A compound of formula II comprising greater than 70% by weight of the R or S enantiomer, in free form or in a pharmaceutically acceptable salt form for use as a pharmaceutical, e.g. in any of the methods as indicated under 1.1 or 1.2 above.

3. A pharmaceutical composition, e.g. for use in any of the methods as in 1.1 or 1.2 above comprising a compound of formula II comprising greater than 70% by weight of the R or S enantiomer in free form or pharmaceutically acceptable salt form in association with a pharmaceutically acceptable diluent or carrier therefor.

4. A compound of formula II comprising greater than 70% by weight of the R or S enantiomer or a pharmaceutically acceptable salt thereof for use in the preparation of a pharmaceutical composition for use in any of the method as in 1.1 or 1.2 above.

The compounds of the invention may be administered as the sole active ingredient or in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders, or a chemotherapeutic agent, e.g a malignant cell anti-proliferative agent. For example, the compounds of the invention may be used in combination with a calcineurin inhibitor, e.g. cyclosporin A or FK 506; a mTOR inhibitor, e.g. rapamycin, 40-O-(2-hydroxyethyl)-rapamycin, CCI779 or ABT578; an ascormycin having immunosuppressive properties, e.g. ABT-281, ASM981, etc.; corticosteroids; cyclophosphamide; azathioprene; methotrexate, leflunomide; mizoribine; mycophenolic acid; mycophenolate mofetil; 15-deoxyspergualine or an immunosuppressive homologue, analogue or derivative thereof; immunosuppressive monoclonal antibodies, e.g., monoclonal antibodies to leukocyte receptors, e.g., MHC, CD2, CD3, CD4, CD7, CD8, CD25, CD28, CD40. CD45, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or a chemotherapeutic agent, e.g. paclitaxel, gemcitabine, cisplatinum, doxorubicin or 5-fluorouracil.

Where the compounds of the invention are administered in conjunction with other immunosuppressive/immunomodulatory, anti-inflammatory or chemotherapeutic therapy, dosages of the co-administered immunosuppressant, immunomodulatory, anti-inflammatory or chemotherapeutic compound will of course vary depending on the type of co-drug employed, e.g. whether it is a steroid or a calcineurin inhibitor, on the specific drug employed, on the condition being treated and so forth. In accordance with the foregoing the present invention provides in a yet further aspect:

5. A method as defined above comprising co-administration, e.g. concomitantly or in sequence, of a therapeutically effective non-toxic amount of a compound of the invention and at least a second drug substance, e.g. an immunosuppressant, immunomodulatory, anti-inflammatory or chemotherapeutic drug, e.g. as indicated above.

6. A pharmaceutical combination, e.g. a kit, comprising a) a first agent which is a compound of the invention as disclosed herein, in free form or in pharmaceutically acceptable salt form, and b) at least one co-agent, e.g. an immunosuppressant, immunomodulatory, anti-inflammatory or chemotherapeutic drug. The kit may comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of the invention and a co-agent, are both administered to a patient simultaneously in the form of a single entity or dosage. The term "non-fixed combination" means that the active ingredients, e.g. a compound of the invention and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

In a further aspect, the present invention provides a method of separating the R and S enantiomers of a compound of formula I, comprising separating the enantiomers by high performance liquid chromatography (HPLC) using a chiral ion-exchange phase e.g. based on quinine carbamate or quinidine carbamate as described above.

In a further aspect, the present invention provides a method of determining the amount of the R and/or S isomers of a compound of formula II present in a sample, comprising (a) reacting the compound of formula II present in the sample with benzene-1,2-dicarbaldehyde to form a compound of formula I, and separating the R and S isomers of the compound of formula I by HPLC. The HPLC is preferably performed as described above, using a chiral ion-exchange phase e.g. based on quinine carbamate or quinidine carbamate. The compounds of formula I are useful as intermediates in such a method. The sample may be e.g. a sample derived from a bodily fluid e.g. blood, plasma, saliva, or urine, and may be first subjected to one or more separation steps, (e.g. extraction with methanol and/or non-chiral HPLC) in order to separate the compound of formula II from the fluid. By such a method the amount of the active R or S enantiomer in the sample may be determined. Thus the method may be useful e.g. for monitoring the blood concentration of the active S enantiomer of a compound of formula II in a subject, following administration of a compound of formula II (e.g. a racemic mixture thereof) or following administration of a precursor of a compound of formula II (forming the compound of formula II as a metabolite in the body) to the subject.

For example, achiral 14C-labeled FTY720 is administered to rats either orally (7.5 mg/kg) or by intravenous infusion (4 mg/kg). Chiral 14C-labeled FTY720-phosphate is formed in the body of the rat as a metabolite of 14C-labeled FTY720. Blood samples are taken at different times (e.g. 3 or 72 hours) after dosing. Each blood sample is extracted with methanol and [14C]FTY720-phosphate is isolated by nonchiral HPLC. The isolated [14C]FTY720-phosphate is derivatized with OPA. The derivative is spiked with unlabelled OPA-derivatized R and S FTY720-phosphate as retention time markers (monitored by UV at 215 nm) and subjected to chiral HPLC separation using a ProntoSIL Chiral AX QN-1 column. The [14C]FTY720-phosphate in all blood samples represents exclusively the pharmacologically active S-enantiomer. The inactive R-enantiomer is not detectable.

The invention claimed is:
1. A process for producing a compound of the formula II

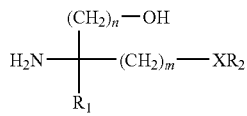   II wherein
each of m and n, independently, is 1, 2 or 3
X is O or a direct bond;
$R_1$ is
a phenylalkyl wherein alkyl is a straight- or branched ($C_{6-20}$)carbon chain; or
a phenylalkyl wherein alkyl is a straight- or branched ($C_{1-30}$)carbon chain wherein said phenylalkyl is substituted at the phenyl residue by
a straight- or branched ($C_{6-20}$)carbon chain optionally substituted by halogen,
a straight- or branched ($C_{6-20}$)alkoxy chain optionally substituted by halogen,
a straight- or branched ($C_{6-20}$)alkenyloxy,
phenylalkoxy, halophenylalkoxy, phenylalkoxyalkyl, phenoxyalkoxy or phenoxyalkyl,
cycloalkylalkyl substituted by $C_{6-20}$alkyl,
heteroarylalkyl substituted by $C_{6-20}$alkyl,
heterocyclic $C_{6-20}$alkyl or
heterocyclic alkyl substituted by $C_{2-20}$alkyl,
and wherein
the alkyl moiety may have
in the carbon chain, a bond or a heteroatom selected from a double bond, a triple bond, O, S, sulfinyl, sulfonyl, or $NR_5$, wherein $R_5$ is H, alkyl, aralkyl, acyl or alkoxycarbonyl, and
as a substituent alkoxy, alkenyloxy, alkynyloxy, aralkyloxy, acyl, alkylamino, alkylthio, acylamino, alkoxycarbonyl, alkoxycarbonylamino, acyloxy, alkylcarbamoyl, nitro, halogen, amino, hydroxy or carboxy, and
$R_2$ is

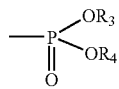

wherein each of $R_3$ and $R_4$, independently, is H or $C_{1-4}$alkyl, wherein alkyl optionally substituted by 1, 2 or 3 halogen atoms; or a pharmaceutically acceptable salt thereof; and wherein greater than 70% of the compound by weight is in the form of the R or S enantiomer;
comprising deprotecting a compound of formula III, IIIa or IIIb wherein greater than 70% by weight of the compound of formula III, IIIa or IIIb is in the form of the R or S enantiomer

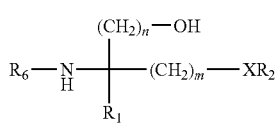   III

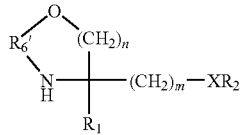   IIIa

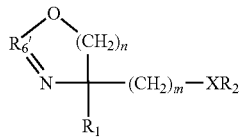   IIIb wherein n, m, X, $R_1$ and $R_2$ are as defined above, $R_6$ is an amino protecting group, and $R_6'$, is an amino protecting group such that $R_6'$, together with the oxygen and nitrogen atoms to which it is attached, the asymmetric carbon atom and 1 to 3 additional carbon atoms forms a 5 to 7 membered heterocyclic ring;
and, where required, converting the compounds of formula II obtained in free form into the salt form, or vice versa.

2. The process according to claim 1 wherein the compound of formula II is phosphoric acid mono-[2-amino-2-hydroxymethyl-4-(4-octyl-phenyl)-butyl]ester or phosphoric acid mono-[2-hydroxymethyl-4-(4-octyl-phenyl)-2-(1-oxo-1,3-dihydro-isoindol-2-yl)-butyl]ester.

3. A process for obtaining a compound of formula III, IIIa or IIIb, as defined in claim 1, wherein greater than 70% of the compound by weight is in the form of the R or S enantiomer, comprising separating the S enantiomer from the R enantiomer in a racemic mixture of a compound of formula III, IIIa or IIIb using chromatography or simulated moving bed chromatography with a polysaccharide-based chiral stationary phase.

4. The process according to claim 3 wherein the stationary phase is amylose-type phase.

5. A process for obtaining a compound of formula III, IIIa or IIIb, as defined in claim 1, wherein greater than 70% of the compound by weight is in the form of the R or S enantiomer, comprising the steps of
i) obtaining a compound of formula IV, IVa or IVb, wherein greater than 70% of the compound by weight is in the form of the R or S enantiomer

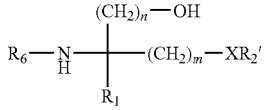   IV

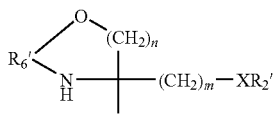   IVa

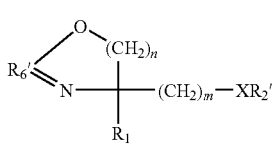   IVb wherein
each of m and n, independently, is 1, 2 or 3
X is O or a direct bond $R_1$ is
- a phenylalkyl wherein alkyl is a straight- or branched ($C_{6-20}$)carbon chain; or
- a phenylalkyl wherein alkyl is a straight- or branched ($C_{1-30}$)carbon chain wherein said phenylalkyl is substituted at the phenyl residue by
  - a straight- or branched ($C_{6-20}$)carbon chain optionally substituted by halogen,
  - a straight- or branched ($C_{6-20}$)alkoxy chain optionally substituted by halogen,
  - a straight- or branched ($C_{6-20}$)alkenyloxy,
  - phenylalkoxy, halophenylalkoxy, phenylalkoxyalkyl, phenoxyalkoxy or phenoxyalkyl,
  - cycloalkylalkyl substituted by $C_{6-20}$alkyl,
  - heteroarylalkyl substituted by $C_{6-20}$alkyl,
  - heterocyclic $C_{6-20}$alkyl or
  - heterocyclic alkyl substituted by $C_{2-20}$alkyl, and wherein
the alkyl moiety may have
- in the carbon chain, a bond or a heteroatom selected from a double bond, a triple bond, O, S, sulfinyl, sulfonyl, or $NR_5$, wherein $R_5$ is H, alkyl, aralkyl, acyl or alkoxycarbonyl, and
- as a substituent alkoxy, alkenyloxy, alkynyloxy, aralkyloxy, acyl, alkylamino, alkylthio, acylamino, alkoxycarbonyl, alkoxycarbonylamino, acyloxy, alkylcarbamoyl, nitro, halogen, amino, hydroxy or carboxy, and $R'_2$ is

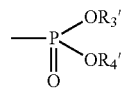

wherein each of $R_3'$ and $R_4'$ is a hydrolysable group and optionally form together a cyclic system, $R_6$ is an amino protecting group, and $R_6'$ is an amino protecting group such that $R_6'$, together with the oxygen and nitrogen to which it is attached, the asymmetric carbon atom and from 1 to 3 additional carbon atoms, forms a 5 to 7 membered heterocyclic ring; and ii) removing the hydrolysable groups present in $R'_2$.

6. The process according to claim 5 wherein $R_3'$ and $R_4'$ form together a cyclic system.

7. A process according to claim 1 wherein $R_6'$ is —C(O)— and the compound that is deprotected is a compound of formula IIIa.

8. A process according to claim 5 wherein $R_6'$ is —C(CH$_3$)— and the compound that is deprotected is a compound of formula IIIb.

* * * * *